(12) United States Patent
Itoh

(10) Patent No.: US 6,565,809 B1
(45) Date of Patent: May 20, 2003

(54) SPECIMEN PROCESSING SYSTEM

(76) Inventor: Teruaki Itoh, 5-25, Kokaihommachi, Kumamoto-shi, Kumamoto-ken (JP)

( * ) Notice: Subject to any disclaimer, the term of this patent is extended or adjusted under 35 U.S.C. 154(b) by 230 days.

(21) Appl. No.: 09/691,884

(22) Filed: Oct. 20, 2000

(30) Foreign Application Priority Data

Oct. 29, 1999 (JP) .......................................... 11-310163

(51) Int. Cl.[7] ........................ G01N 21/00; G01N 31/00; G01N 33/00; G01N 9/30; B01L 3/02; B01L 11/00; G05B 1/00; B01D 21/30; B01D 24/32; B01D 33/00; B01D 21/26

(52) U.S. Cl. ......................... 422/67; 422/68.1; 422/72; 422/73; 422/100; 422/101; 422/105; 422/107; 494/1; 494/10; 210/739; 210/781; 210/143; 210/194; 210/360.1; 210/512.1

(58) Field of Search ........................ 422/67, 68.1, 72, 422/73, 99, 100, 101, 105, 107; 210/360.1, 380.1, 787, 512.1, 739, 745, 143, 96.1, 194; 494/1, 10

(56) References Cited

U.S. PATENT DOCUMENTS

| | | | | | |
|---|---|---|---|---|---|
| 3,635,394 A | * | 1/1972 | Natelson | ....................... | 422/65 |
| 3,778,232 A | * | 12/1973 | McMorrow, Jr. | .............. | 211/74 |
| 4,022,579 A | * | 5/1977 | Revillet et al. | ............... | 211/74 |
| 4,828,716 A | * | 5/1989 | McEwen et al. | ............ | 210/104 |
| 5,322,192 A | * | 6/1994 | Godolphin et al. | ......... | 222/479 |
| 5,578,269 A | * | 11/1996 | Yaremko et al. | ............ | 210/361 |
| 5,733,446 A | * | 3/1998 | Holm | ......................... | 210/206 |
| 5,814,276 A | * | 9/1998 | Riggs | ........................ | 422/100 |
| 5,824,230 A | * | 10/1998 | Holm et al. | ................ | 210/749 |
| 5,935,432 A | * | 8/1999 | Holm | ......................... | 210/206 |
| 5,955,026 A | * | 9/1999 | Holm et al. | ................. | 422/55 |
| 5,980,734 A | * | 11/1999 | Itoh | .......................... | 210/518 |
| 6,060,022 A | * | 5/2000 | Pang et al. | ................... | 422/63 |
| 6,063,297 A | * | 5/2000 | Antanavich et al. | ... | 210/321.67 |
| 6,099,740 A | * | 8/2000 | Holm | ........................ | 210/143 |
| 6,290,907 B1 | * | 9/2001 | Takahashi et al. | .......... | 422/100 |
| 6,318,191 B1 | * | 11/2001 | Chen | ........................ | 422/68.1 |
| 6,337,050 B1 | * | 1/2002 | Takahashi et al. | ............ | 422/63 |
| 2001/0007315 A1 | * | 7/2001 | Fiehler | ....................... | 210/787 |

* cited by examiner

*Primary Examiner*—Jill Warden
*Assistant Examiner*—B. R. Gordon
(74) *Attorney, Agent, or Firm*—Nixon & Vanderhye

(57) ABSTRACT

The present invention provides a specimen processing system for centrifuging a specimen such as blood and then dispensing the specimen. This system comprises a dispense error specimen removing unit for removing a specimen in which a dispense error has been caused due to a fibrin in a dispense process, a feedback unit for injecting fibrin-decomposing beads into the specimen removed by the dispense error specimen removing unit and feeding the specimen containing the beads back to a centrifuge process, a reprocess control unit for causing the specimen fed back to the centrifuge process by the feedback unit to be centrifuged again, and a system controller for automatically controlling the dispense error specimen removing unit, the feedback unit, and the reprocess control unit.

1 Claim, 2 Drawing Sheets

SPECIMEN PROCESSING SYSTEM

CROSS-REFERENCE TO RELATED APPLICATIONS

This application is based upon and claims the benefit of priority from the prior Japanese Patent Application No. 11-310163, filed Oct. 29, 1999, the entire contents of which are incorporated herein by reference.

BACKGROUND OF THE INVENTION

The present invention relates to a specimen processing system for subjecting a specimen such as blood to a centrifugal process, a dispense process and the like.

When an operator extracts serum from collected blood, he or she generally centrifuges a master specimen constituted of both blood and a silicon separating agent injected into a test tube using a centrifugal unit. In the centrifugal process, a blood clot whose specific gravity is relatively high is separated below the separating agent, and serum whose specific gravity is relatively low is separated above the separating agent.

The serum so obtained is dispensed in a dispensing unit. This dispense process is generally performed as follows. The serum is absorbed and extracted from the test tube through an air suction nozzle having a disposable dispensing TIP at the tip thereof, and the extracted serum is separately injected into a plurality of slave specimen containers (such as test tubes), with the result that a plurality of slave specimens can be obtained.

There is a case where soft fiber materials such as a so-called fibrin are caused in a serum layer of a master specimen which has been centrifuged. If the fibrin is mixed in the serum layer, it is likely to be adhered to the tip of the dispensing TIP when the dispense process is executed by the dispensing unit. Thus, an opening of the tip of the dispense TIP is clogged or the fibrin is mixed into the slave specimens, with the result that the dispense process is not performed normally or a so-called dispense error occurs.

Conventionally, an operator has taken the following measures against the above-described dispense error. When a dispense error is caused by a fibrin, an operator intermits the dispense process and takes out a test tube including a specimen causing the dispense error. He or she injects beads for decomposing the fibrin into the test tube and carries them to the centrifugal unit by hand. The operator centrifuges the carried specimen again and restarts the dispense process.

In the conventional specimen processing system described above, an operator manually performed a series of operations of taking out a specimen causing a dispense error, injecting beads into the specimen, and centrifuging the specimen again. It was therefore difficult for the operator to carry out the operations quickly and exactly. Moreover, the intermittence of the dispense process stopped the flow of the specimen processing operation and decreased the operation efficiency.

BRIEF SUMMARY OF THE INVENTION

The object of the present invention is to provide a specimen processing system having the following advantages:

1) When a dispense error is caused due to fibrin in a dispense process, the specimen is automatically centrifuged again and no special operator's manual operation is required. The specimen can thus quickly and exactly be centrifuged again; and 2) When a specimen in which a dispense error has occurred is centrifuged again, the dispense processing need not be intermitted, so that there is no fear that the flow of the specimen processing will be stopped.

To attain the above object, the specimen processing system according to the present invention is characterized chiefly by the following structure. The other characteristic structures will be clarified in the Detailed Description of the Invention.

The specimen processing system of the present invention, for centrifuging a specimen such as blood and then dispensing the specimen, comprises a dispense error specimen removing unit for removing a specimen in which a dispense error has been caused due to a fibrin in a dispense process, a feedback unit for injecting fibrin-decomposing beads into the specimen removed by the dispense error specimen removing unit and feeding the specimen back to a centrifuge process, and a reprocess control unit for causing the specimen fed back to the centrifuge process by the feedback unit to be centrifuged again.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Embodiment

Figure 1:
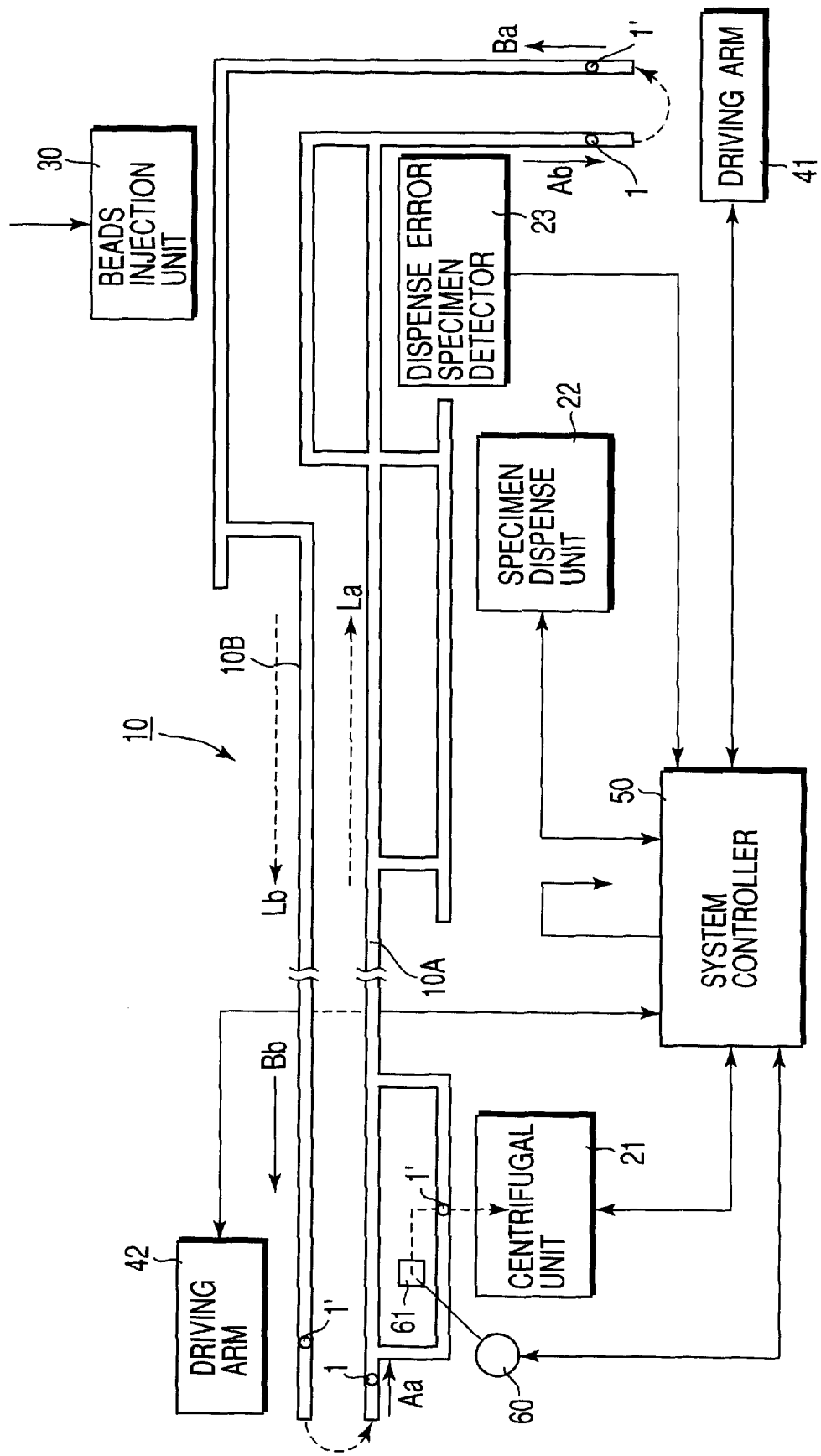
FIG. 1 is a block diagram showing a configuration of a specimen processing system according to an embodiment of the present invention.
Figure 2:
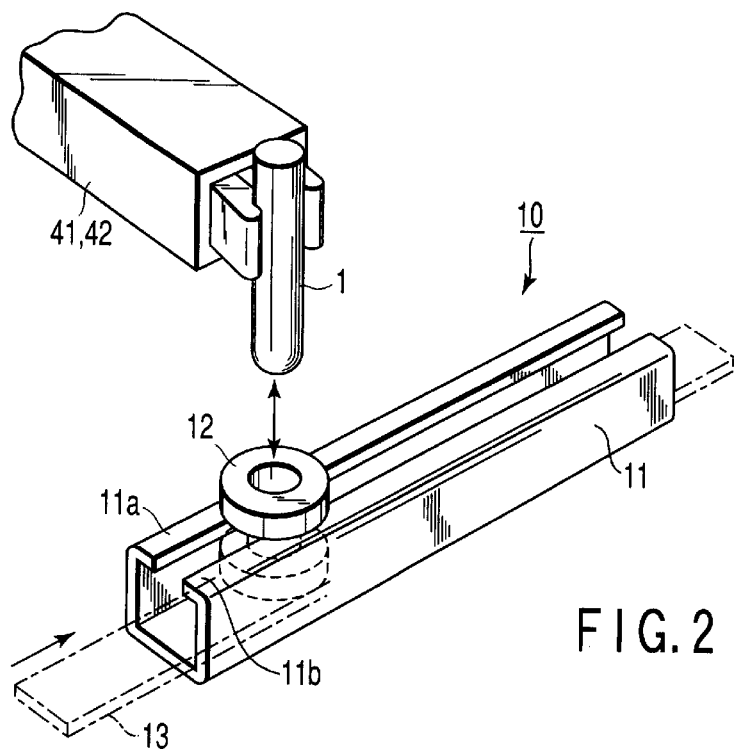
FIG. 2 is a perspective view showing a basic structure of a specimen transfer lane according to the embodiment of the present invention.

In FIG. 1, reference numeral 10 indicates a specimen transfer lane. As FIG. 2 shows a basic structure of the specimen transfer lane 10, the lane 10 includes a lane body 11 having guide rails 11a and 11b on both sides of the lane 10, a cylindrical specimen container holder 12 guided and moved in the longitudinal direction of the lane body 11 by the guide rails 11a and 11b and having a hollow for holding a specimen container 1, such as a test tube including a specimen, in its core, and a conveyor belt 13 for conveying the specimen container holder 12 in the longitudinal direction of the lane body 11.

The specimen container 1 can be inserted into and removed from the specimen container holder 12 by driving arms 41 and 42 (which will be described later) at the appropriate times.

Returning to FIG. 1, the specimen transfer lane 10 is constituted of a main transfer lane 10A and a sub-transfer lane 10B arranged in parallel with each other. The main transfer lane 10A is so provided that the specimen container 1 containing a specimen such as blood can be transferred along a process line La in the directions indicated by arrows Aa and Ab. The sub-transfer lane 10B is arranged in parallel with the main transfer lane 10A and so provided that the specimen container 1 can be transferred along a feedback line Lb in the directions opposed to the process line La or indicated by arrows Ba and Bb.

A centrifugal unit 21, a specimen dispense unit 22, and a dispense error specimen detector 23 are arranged by the side of the main transfer lane 10A and almost along the process line La. A beads injection unit 30 is disposed by the side of the sub-transfer lane 10B. The driving arm 41 is provided as a first moving mechanism in a slightly downstream position from the dispense error specimen detector 23. The second driving arm 42 is provided as a second moving mechanism in a slightly upstream position from the centrifugal unit 21.

The centrifugal unit 21, specimen dispense unit 22, dispense error specimen detector 23, beads injection unit 30, and driving arms 41 and 42 are controlled by a system controller 50 serving as an automatic control means.

Though not shown, various devices and units are arranged in addition to those described above.

The centrifugal unit 21 receives the specimen container 1 containing a master specimen from the main transfer lane 10A along the process line La and centrifuges the specimen. When the specimen is blood, the container 1 contains collected blood and a silicon separating agent. A plurality of specimen containers 1 are loaded together into the centrifugal unit 21. They are centrifuged at once by the unit 21 and then removed therefrom.

The dispense unit 22 receives the specimen container 1 containing the master specimen, which has been centrifuged by the centrifugal unit 21 and then transferred through the main transfer lane 10A, and performs a dispense process for the specimen container 1, thereby obtaining a plurality of slave specimens. This dispense process is usually performed as follows. Generally, serum is absorbed and extracted from the specimen container 1 by means of an air suction nozzle having a disposable dispense TIP (not shown) at the tip thereof, and the extracted serum is separately injected into a plurality of slave specimen containers (such as test tubes).

When a dispense error is caused in a specimen due to fibrin in the dispense process of the dispense process unit 22, the dispense error specimen detector 23 detects the specimen.

The driving arm 41 serving as the first moving mechanism is constituted of a robot arm. The arm 41 catches a specimen container 1' containing a dispense error specimen detected by the dispense error specimen detector 23, removes it from the main transfer lane 10A, and moves it to the sub-transfer lane 10B. In other words, the specimen container 1' is pulled out of the specimen container holder 12 of the main transfer lane 10A by the driving arm 41 and inserted into the holder 12 of the sub-transfer lane 10B. The specimen container 1' is therefore transferred in the direction of the centrifugal unit 21 along the feedback line Lb, as indicated by arrow Ba.

When the specimen container 1' is transferred to the position of the beads injection unit 30, the unit 30 catches the container and injects beads therein.

Figure 3:
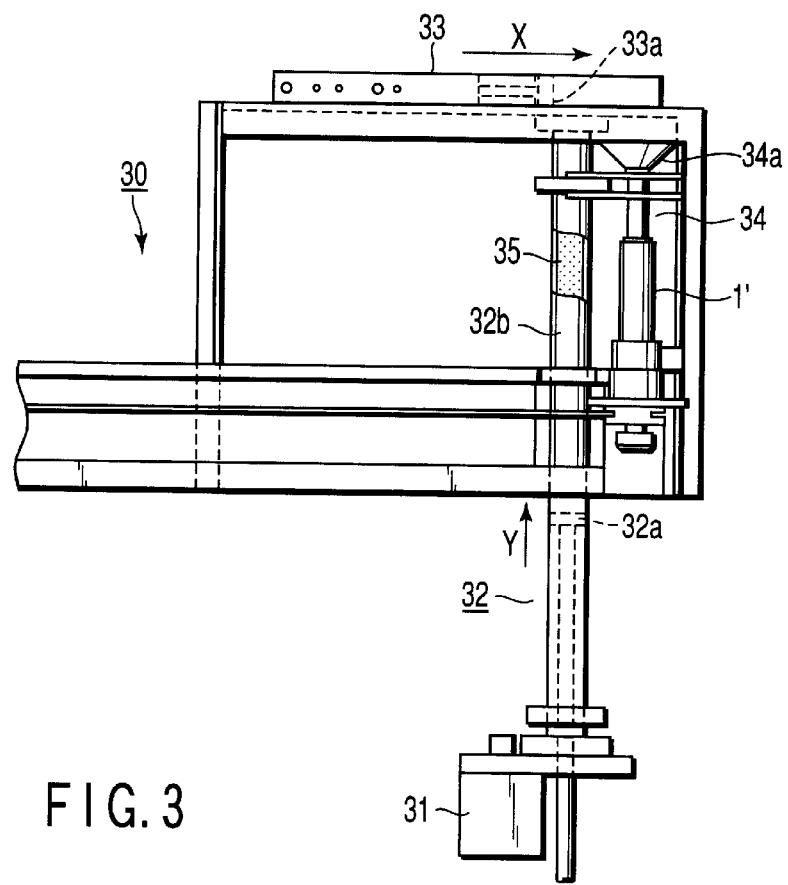
FIG. 3 is a side view showing a specific example of the structure of a beads injection unit according to the embodiment of the present invention.

FIG. 3 is a side view showing a specific example of the structure of the beads injection unit 30. As shown in FIG. 3, the beads injection unit 30 comprises a motor 31, a beads push-out mechanism 32 constituted of a piston/cylinder device, a beads feed mechanism 33 constituted of a piston/ cylinder device, and a beads guide mechanism 34 having a funnel section 34a. Beads 35 are held in a cylinder 32b of the beads push-out mechanism 32 in advance.

If the motor 31 rotates to lift a piston 32a of the beads push-out mechanism 32 to a predetermined level as indicated by arrow Y, the beads 35 are pushed out of the cylinder 32b toward the top of the unit by a given amount corresponding to the level of lift of the piston 32a. When the beads feed mechanism 33 operates, the beads 35 pushed toward the top of the unit are fed by a piston 33a of the mechanism 33 in the horizontal direction as indicated by arrow X and then guided into the bead guide mechanism 34 through the funnel section 34a. Consequently, the beads 35 are injected into the specimen container 1' containing a dispense error specimen which has been caught in the unit 30 through the beads guide mechanism 34.

Returning to FIG. 1, the driving arm 42 serving as the second moving mechanism moves the specimen container 1' containing a dispense error specimen, which has been transferred to the upstream side of the centrifugal unit 21 through the sub-transfer lane 10B after the beads are injected by the beads injection unit 30, to the main transfer lane 10A again. In other words, the specimen container 1' is pulled out of the specimen container holder 12 of the sub-transfer lane 10B by the driving arm 42 and inserted into the specimen container holder 12 of the main transfer lane 10A. Thus, the specimen container 1' is transferred to the vicinity of the centrifugal unit 21 again along the process line La. The specimen container 1' is centrifuged again by the centrifugal unit 21 through a reprocess control unit 60. The reprocess control unit 60 includes a priority process unit 61 for causing the specimen container 1' containing a dispense error specimen to be centrifuged prior to the centrifuge of the other specimen container 1. The series of operations described above is automatically performed by the system controller 50.

Features of the Embodiment

[1] A specimen processing system according to the above embodiment, for centrifuging a specimen such as blood and then dispensing the specimen, comprises a dispense error specimen removing unit (23, 41) for removing a specimen in which a dispense error has been caused due to a fibrin in a dispense process, a feedback unit (30, 42) for injecting fibrin-decomposing beads (35) into the specimen removed by the dispense error specimen removing unit (23, 41) and feeding the specimen back to a centrifuge process, and a reprocess control unit (60) for causing the specimen fed back to the centrifuge process by the feedback unit (30, 42) to be centrifuged again.

[2] A specimen processing system according to the above embodiment, comprises a main transfer lane (10A) provided so as to transfer a specimen such as blood in a direction of a process line, a sub-transfer lane (10B) provided in parallel with the main transfer lane (10A) so as to transfer the specimen in a direction opposite to that of the process line, a centrifugal unit (21) for centrifuging a master specimen transferred through the main transfer lane (10A), a dispensing unit (22) for dispensing the master specimen, which has been centrifuged by the centrifugal unit (21) and then transferred through the main transfer lane (10A), into a plurality of slave specimens, a dispense error specimen detector (23) for detecting a dispense error specimen in which a dispense error is caused due to a fibrin in a dispense process executed by the dispensing unit (22), a first moving mechanism (41) for moving the dispense error specimen detected by the dispense error specimen detector (23) to the sub-transfer lane (10B), a beads injection unit (30) for injecting fibrin-decomposing beads (35) into the dispense error specimen moved to the sub-transfer lane (10B) by the first moving mechanism (41), a second moving mechanism (42) for moving the dispense error specimen, into which the beads (35) have been injected and which have been transferred through the sub-transfer lane (10B), to the main transfer lane (10A) again, and a reprocess control unit (60) for causing the centrifugal unit (21) to centrifuge the dispense error specimen which has been moved to the main transfer lane (10A) by the second moving mechanism (42) and then transferred through the main transfer lane (10A) again.

[3] In the specimen processing system according to the above paragraph [2], the reprocess control unit (60) includes a priority process unit (61) for causing the dispense error specimen to be centrifuged prior to a centrifuge of another specimen.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A specimen processing system comprising:
   - a main transfer lane provided so as to transfer a blood specimen in a direction of a process line;
   - a sub-transfer lane provided in parallel with the main transfer lane so as to transfer the specimen in a direction opposite to that of the process line;
   - a centrifugal unit for centrifuging a master specimen transferred through the main transfer lane;
   - a dispensing unit for dispensing the master specimen, which has been centrifuged by the centrifugal unit and then transferred through the main transfer lane, into a plurality of slave specimens;
   - a dispense error specimen detector including a sensor for detecting a master specimen in which a dispense error has been caused due to a fibrin in a dispense process executed by the dispensing unit;
   - a first moving mechanism including a first driving arm provided in a slightly downstream position from the dispense error specimen detector, the first driving arm catching the dispense error specimen detected by the dispense error specimen detector and moving the caught specimen from the main transfer lane to the sub-transfer lane;
   - a beads injection unit provided by the side of the sub-transfer lane, including a beads push-out mechanism for pushing out a predetermined amount of beads for a fibrin decomposing process and a beads feed mechanism for injecting the beads pushed out by the beads push-out mechanism into the dispense error specimen transferred to the sub-transfer lane by the first moving mechanism;
   - a second moving mechanism including a second driving arm provided in an upstream position from the centrifugal unit, the second driving arm catching the dispense error specimen, into which the beads have been injected by the beads injecting unit and which has been transferred through the sub-transfer lane, to move the caught specimen from the sub-transfer lane to the main transfer lane again;
   - a reprocess control unit for causing the centrifugal unit to centrifuge the dispense error specimen which has been moved to the main transfer lane by the second moving mechanism and then transferred through the main transfer lane again, the reprocess control unit including a priority processing unit for causing the dispense error specimen to be centrifuged prior to a centrifuge of another specimen, and
   - a system controller for automatically controlling at least the centrifugal unit, dispense unit, dispense error specimen detector, beads injection unit, first and second moving mechanisms and reprocess control unit.

* * * * *